(12) United States Patent
Kim et al.

(10) Patent No.: US 7,815,860 B2
(45) Date of Patent: Oct. 19, 2010

(54) BIOSENSOR, BIOSENSOR SYSTEM AND METHOD OF USING THEREOF

(75) Inventors: Young-il Kim, Suwon-si (KR); Jung-ho Kang, Suwon-si (KR); Tae-sik Park, Suwon-si (KR)

(73) Assignee: Samsung Electronics Co., Ltd. (KR)

( * ) Notice: Subject to any disclaimer, the term of this patent is extended or adjusted under 35 U.S.C. 154(b) by 0 days.

(21) Appl. No.: 11/286,030

(22) Filed: Nov. 23, 2005

(65) Prior Publication Data

US 2006/0205060 A1 Sep. 14, 2006

(30) Foreign Application Priority Data

Jan. 11, 2005 (KR) .................... 10-2005-0002406

(51) Int. Cl.
*G01N 25/20* (2006.01)
*G01N 27/00* (2006.01)
*G01N 33/00* (2006.01)
*G01N 33/48* (2006.01)
*G01N 33/50* (2006.01)
*G01N 33/53* (2006.01)

(52) U.S. Cl. ................. 422/82.01; 422/68.1; 422/82.02; 422/82.05; 435/4; 435/6; 435/7.1; 435/287.2; 435/287.9; 435/288.3; 436/147

(58) Field of Classification Search ............. 435/4, 435/6, 7.1, 287.2, 287.9, 288.3; 422/68.1, 422/82.01–82.02, 82.05; 436/147
See application file for complete search history.

(56) References Cited

U.S. PATENT DOCUMENTS

| 4,142,161 | A * | 2/1979 | Gray ............. 331/116 FE |
|---|---|---|---|
| 4,454,481 | A * | 6/1984 | Lewis ................ 330/307 |
| 5,008,541 | A * | 4/1991 | Audaire et al. ........ 250/338.3 |
| 5,017,494 | A * | 5/1991 | Karube et al. .......... 435/287.9 |
| 5,846,708 | A * | 12/1998 | Hollis et al. ............ 435/6 |
| 6,326,563 | B1 * | 12/2001 | Takeuchi et al. ........ 177/210 FP |
| 6,457,361 | B1 * | 10/2002 | Takeuchi et al. ........ 73/580 |
| 6,663,834 | B1 * | 12/2003 | Miller et al. .......... 422/94 |
| 2002/0189375 | A1 * | 12/2002 | Takeuchi et al. ........ 73/865 |
| 2004/0053435 | A1 * | 3/2004 | Ikushima et al. ........ 438/57 |
| 2004/0078219 | A1 * | 4/2004 | Kaylor et al. .......... 705/2 |

FOREIGN PATENT DOCUMENTS

JP 02297026 A * 12/1990
KR 2001090642 A * 10/2001

* cited by examiner

*Primary Examiner*—Unsu Jung
(74) *Attorney, Agent, or Firm*—Cantor Colburn LLP

(57) ABSTRACT

A biosensor for detecting an analyte by using a variable voltage according to infrared radiation absorption is provided. The biosensor includes an infrared absorber having a variable resistance and bioreceptors immobilized onto the infrared absorber for selectively reacting and binding with an analyte, wherein an induced voltage at the infrared absorber varies depending on whether the bioreceptor reacts and binds with the analyte.

23 Claims, 4 Drawing Sheets

BIOSENSOR, BIOSENSOR SYSTEM AND METHOD OF USING THEREOF

This application claims priority to Korean Patent Application No. 2005-002406, filed on Jan. 11, 2005, and all the benefits accruing therefrom under 35 U.S.C. §119, the entire contents of which are incorporated herein by reference in its entirety.

BACKGROUND OF THE INVENTION

1. Field of the Invention

The present invention relates to a biosensor and a biosensor system, and further to a method of using the biosensor and biosensor system to detect a target object in a sample.

2. Description of the Related Art

In general, a biosensor is a device that uses a specific biological element or a physical element similar to the biological element to get information from a target object to be measured (i.e., analyte). The detected information is usually transduced by the biosensor into recognizable signals such as colors, fluorescence or electrical signals. With technical advances in modem science, the biosensor is one of the devices that have been developed rapidly.

The application fields of the biosensor are largely divided into six categories. Firstly, biosensors are used mostly in medical field (clinical diagnosis) such as the measurement of blood glucose levels. Besides the measurement of blood glucose levels, the biosensors available in the market or under development analyze and diagnose diverse biomasses including lactic acid, cholesterol, urea and the like. Secondly, biosensors are used for environment applications. In effect, ever increasing needs for environment monitoring will speed up the development of an environment monitoring biosensor. For instance, biosensors are already used to detect biochemical oxygen demand (BOD), cyanide, phenol, heavy metals, pesticides, phosphorus compounds, and nitrogen compounds in sewage. Thirdly, biosensors are used in the field of food safety risk analysis in connection with pesticide residues in food, antibiotics, pathogenic bacteria and other toxic chemical compounds. Fourthly, biosensors are used for military purposes such as in a biochemical weapon sensing biosystem. Since the biochemical weapon sensing must be done very speedily, the biosensor must perform quickly and used frequently. Fifthly, biosensors are used for the analysis of specific chemical substances used in industrial processes including pharmaceutical, chemical, petrochemical processes and so forth. Biosensors are used widely in the fermentation processes of biological industries. Lastly, biosensors are used in laboratories conducting experimental research. In this case, biosensors have special usages and structures. General biosensors are usually built in small sizes allowing for carrying or transport and utilized to analyze specific substances in a real time mode. However, the biosensors for use in experiments are not limited by size, but by analytical capabilities with respect to kinetic analysis on bonding between biomasses, single molecular behavior measurement, and the like.

The biosensor is composed of a bioreceptor which reacts or binds with a specific substance to be detected (i.e., analyte), and a signal transducer which transfers a signal generated by the reaction between the bioreceptor and the analyte. Examples of the bioreceptor include an enzyme, antibody, antigen, membrane, receptor, cell, tissue, and deoxyribonucleic acid (DNA), which selectively reacts and bonds with the analyte. As for the signal transducing method, a variety of physicochemical methods such as electrochemical, fluorescence, color, optical, piezoelectric and SPR (Surface plasmon resonance) are used.

In detail, the optical signal transduction uses a chromogen which changes color at the reaction with oxidase (or bioreceptor). Thus, when a bioreceptor reacts with an analyte, i.e., glucose, the degree of color change in the chromogen is measured. Here, the degree of color change is measured in terms of optical reflectivity or transmittance using a photometer to detect glucose. The electrochemical signal transduction transfers the electrons generated from the oxidation of glucose to an electrode using an electron transfer medium, and measures current flowing through the electrode to detect glucose in blood. According to the signal transduction using fluorescence and color, a label showing fluorescence or color during the reaction between a bioreceptor and an analyte is used. This fluorescence or color development is detected by a laser. Meanwhile, the SPR technology does not use a label material. As its name implies, the SPR uses the surface plasmon resonance phenomenon. More specifically, it monitors, in real-time mode, specific reactions, binding, affinity and kinetic elements between molecules in response to a change in the SPR angle. Lastly, the typical example of the piezoelectric signal transduction is QCM (quartz crystal microbalance). According to the QCM, a metal electrode is attached to both sides of a quartz crystal, and a voltage is impressed thereto. Then, the quartz crystal starts vibrating. This phenomenon is called inverse piezoelectric effect. If a foreign substance is attached to the surfaces of the electrodes, the quartz crystal vibration property is changed. By measuring this change, it becomes possible to observe the movement of the foreign substance on the surfaces of the electrodes.

The above-described signal transducing methods show general similitudes, that is, they detect the reaction or binding between a bioreceptor like enzyme or antibody and an analyte. However, biosensors based on these methods are not economical in that they are applied to specific bioreceptors only, the equipment can be large, or expensive color development reagent or laser are required. Especially, it is difficult to commercialize the methods using a label material because the label material itself and the equipment for detecting the label material are both very expensive.

SUMMARY OF THE INVENTION

The present invention provides a biosensor and a biosensor system that may be applied to almost every kind of bioreceptor and do not require a label material.

In an exemplary embodiment, a biosensor includes an infrared absorber having a variable resistance; and bioreceptors immobilized onto the infrared absorber for selectively reacting and binding with an analyte, wherein, an induced voltage at the infrared absorber varies depending on whether the bioreceptor reacts and binds with the analyte.

In another exemplary embodiment, the biosensor further includes a voltage amplifying part connected to the infrared absorber, for amplifying the induced voltage at the infrared absorber. The voltage amplifying part may be a MOSFET or Bipolar transistor.

In another exemplary embodiment, the infrared absorber is Ti (titanium).

In another exemplary embodiment, the bioreceptor includes enzyme, antibody, antigen, membrane, receptor, cell, tissue and DNA.

Another exemplary embodiment of the present invention provides a biosensor, including: a substrate; a plurality of infrared absorbers formed on the substrate; a plurality of bioreceptors immobilized onto the infrared absorbers for selectively reacting and binding with different analytes; and a plurality of voltage amplifying parts connected to the plurality of the infrared absorbers, for amplifying an induced voltage at each infrared absorber, wherein an induced voltage at the infrared absorber varies depending on whether the different kinds of bioreceptors react and bind with the analytes, respectively.

Another exemplary embodiment of the present invention provides a biosensor system, including: an infrared generator; a biosensor which includes an infrared absorber having a variable resistance according to the amount of absorbing infrared radiation emitted from the infrared generator, and bioreceptors immobilized onto the infrared absorber for selectively reacting and binding with an analyte, wherein an induced voltage at the infrared absorber varies depending on whether the bioreceptor reacts and binds with the analyte; and an output unit for displaying an induced voltage at the biosensor.

In an exemplary method according to the present invention, a method of detecting a target object is provided, the method including coating a sample on a biosensor, irradiating the surface of the biosensor, measuring an output voltage induced at the biosensor and comparing the output voltage to a reference voltage to determine whether the target object is contained in the sample. When the output voltage is difference than the reference voltage, the target object is detected in the sample.

The biosensor and the biosensor system according to the present invention can be advantageously used in that they are capable of easily detecting an analyte without using a label material, by detecting an induced voltage at the sensor after the infrared irradiation and comparing the induced voltage being detected with a reference voltage to decide whether a bioreceptor has reacted and bound with the analyte.

Also, since the biosensor and the biosensor system of the present invention detects an analyte based on the change in voltage that varies depending on the infrared radiation absorption, they can be applied to almost all kinds of bioreceptors.

BRIEF DESCRIPTION OF THE DRAWINGS

The above aspects and features of the present invention will be more apparent by describing certain embodiments of the present invention with reference to the accompanying drawings, in which.

DETAILED DESCRIPTION OF THE INVENTION

Figure 1:
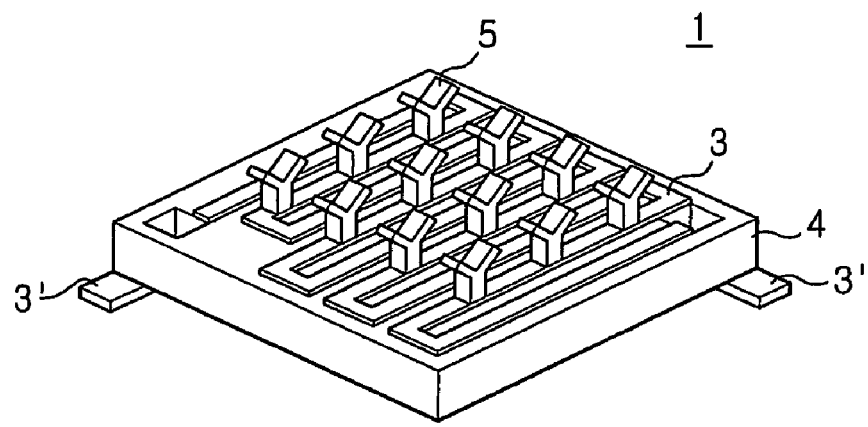
FIG. 1 is a schematic view illustrating an exemplary embodiment of a biosensor, in accordance with the present invention.

The invention is described more fully hereinafter with reference to the accompanying drawings, in which exemplary embodiments of the invention are shown. This invention may, however, be embodied in many different forms and should not be construed as limited to the exemplary embodiments set forth herein. Rather, these embodiments are provided so that this disclosure will be thorough and complete, and will fully convey the scope of the invention to those skilled in the art. In the drawings, the size and relative sizes of layers and regions may be exaggerated for clarity.

It will be understood that when an element or layer is referred to as being "on" or "connected to" another element or layer, the element or layer can be directly on or connected to another element or layer or intervening elements or layers. In contrast, when an element is referred to as being "directly on" or "directly connected to" another element or layer, there are no intervening elements or layers present. Like numbers refer to like elements throughout. As used herein, the term "and/or" includes any and all combinations of one or more of the associated listed items.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Embodiments of the invention are described herein with reference to cross-section illustrations that are schematic illustrations of idealized embodiments (and intermediate structures) of the invention. As such, variations from the shapes of the illustrations as a result, for example, of manufacturing techniques and/or tolerances, are to be expected. Thus, embodiments of the invention should not be construed as limited to the particular shapes of regions illustrated herein but are to include deviations in shapes that result, for example, from manufacturing.

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the relevant art and will not be interpreted in an idealized or overly formal sense unless expressly so defined herein.

Exemplary embodiments of the present invention will be described herein below with reference to the accompanying drawings.

Referring to FIG. 1, an exemplary embodiment of a biosensor 1 according to the present invention includes an infrared absorber 3, and bioreceptors 5.

The infrared absorber 3 may include materials whose resistance varies by the absorption of infrared rays. For instance, if the infrared absorber 3 absorbs infrared rays, voltage is induced, and the infrared absorber 3 resistance value changes by the difference between the amount of infrared radiation absorption when the bioreceptor 5 is not immobilized onto the surface of the infrared absorber 3, the amount of infrared radiation absorption when only the bioreceptor 5 is immobilized onto the surface of the infrared absorber 3 and the amount of infrared radiation absorption when the bioreceptor 5 binds with an analyte (126 in FIG. 6). In exemplary embodiments, the voltage values being induced at the infrared absorber 3 should vary. For example, the infrared absorber 3 may include Ti (titanium). Any material that has varying resistance, and thus has variable voltage values according to the amount of infrared radiation absorption before and after the reaction with the bioreceptor 5 and the binding, may be used for the infrared absorber 3.

As shown in FIG. 1, the infrared absorber 3 is formed substantially in band shape on a sheet (i.e., wafer), and bent in a zigzag pattern on a support plate 4. In this configuration, the infrared absorber 3 having a denser structure is placed in a given small area, so that the change in resistance according to the infrared radiation absorption may be maximized. The infrared absorber 3 may be formed in any shaped configuration suitable for the purpose described herein, of concentrating and efficiently placing the infrared absorber 3 in a small area.

The bioreceptor 5 selectively reacts and binds with a substance to be detected, i.e., an analyte 126, and is immobilized onto the infrared absorber 3. The bioreceptor 5 may include, but is not limited to, an enzyme, antibody, antigen, membrane, receptor, cell, tissue and DNA. Any of a number of different and diverse chemical or physical methods for immobilizing the bioreceptors 5 onto the infrared absorber 3 may be used as is suitable for the purpose described herein.

The following will now explain an exemplary embodiment of the operation of the biosensor, with reference to FIG. 1.

The infrared absorber 3 is formed in the pattern shown in FIG. 1 on the support plate 4. Infrared rays are emitted by means of an infrared generator (110 in FIG. 5), including, but not limited to, an infrared lamp. A voltage is induced at the infrared absorber 3 and is measured. The voltage measurement is performed at the end portions of the infrared absorber 3. Here, the voltage may be referred to as an intrinsic voltage.

Next, the bioreceptor 5 to be reacted and bound with an analyte 126 that the biosensor 1 needs to detect is immobilized onto the infrared absorber 3. For example, in the case of detecting a specific disease using an antigen-antibody reaction, the antigen or the antibody of the target disease is immobilized onto the infrared absorber 3. After disposing the bioreceptor 5 onto the infrared absorber 3 and emitting infrared rays using the infrared generator 110, the voltage induced at the infrared absorber 3 is measured. Here, the voltage may be referred to as an immobilization voltage. Since the bioreceptor 5 is immobilized onto the surface of the infrared absorber 3, the amount of infrared radiation absorbed by the infrared absorber 3 is different from the amount of infrared radiation absorbed where the bioreceptor 5 is not immobilized onto the surface of the infrared absorber 3. In exemplary embodiments, if the bioreceptor 5 is properly immobilized, the immobilization voltage measured at the end portions 3' of the infrared absorber 3 is different from the intrinsic voltage. However, if the immobilization voltage equals to the intrinsic voltage, it means that the bioreceptor 5 is not properly immobilized. The measurement of the immobilization voltage and comparison to the intrinsic voltage indicates whether the bioreceptor 5 is properly immobilized onto the infrared absorber 3. The immobilization voltage value may vary according to the type of bioreceptor 5 used.

A prepared sample reacts with the bioreceptor 5 of the biosensor 1, and infrared rays from the infrared generator 110 are irradiated thereto. The voltage induced across the end portions 3' of the infrared absorber 3 is measured. Here, the voltage measured may be referred to as a reaction voltage. In exemplary embodiments, if the reaction voltage differs from the immobilization voltage, the bioreceptor 5 has reacted and bound with an analyte 126. The bioreceptor 5 reacting and binding with the analyte 126 indicates that the analyte 126 to be detected exists in the sample. The difference in the reaction voltage and immobilization voltage is due to the amount of infrared radiation absorbed by the infrared absorber 3 after the bioreceptor 5 was reacted and bound with the analyte 126 being different from the amount of infrared radiation absorbed by the infrared absorber 3 before the bioreceptor 5 reacts with the analyte 126.

Figure 2:
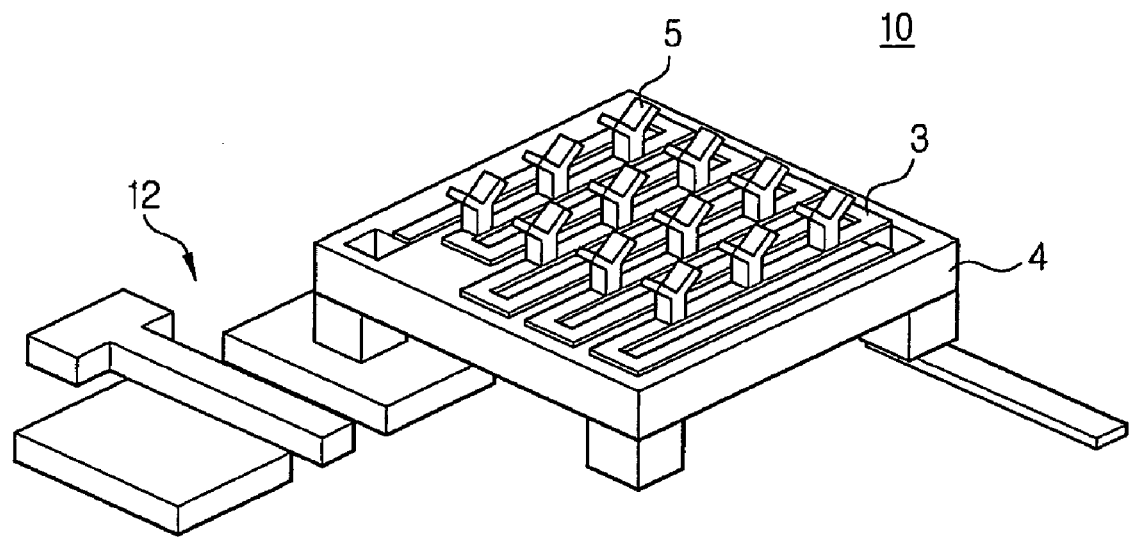
FIG. 2 is a schematic view illustrating another exemplary embodiment of a biosensor, in accordance with the present invention.

FIG. 2 illustrates another exemplary embodiment of the biosensor according to the present invention. Referring to FIG. 2, the biosensor 10 includes an infrared absorber 3 formed on a support plate 4, bioreceptors 5 immobilized onto the infrared absorber 3, and a voltage amplifying part 12.

The functions and structures of the infrared absorber 3 and the bioreceptor 5 are substantially similar with those in the biosensor 1 of FIG. 1.

The voltage amplifying part 12 is connected to one end of the infrared absorber 3. The voltage amplifying part 12 amplifies an induced voltage at the infrared absorber 3 having absorbed infrared radiation. Amplifying the induced voltage at the infrared absorber 3, may make it easier to detect the changes in voltage at the infrared absorber 3 before and after the reaction between the bioreceptor 5 and the analyte 126. For example, when the induced voltage is amplified, the difference in voltages is correspondingly magnified to determine whether the bioreceptor 5 is bound with the analyte 126. Any type of electronic device capable of amplifying voltage may be used for the voltage amplifying part 12. The voltage amplifying part 12 may be implemented with, for example, a metal oxide field effect transistor (MOSFET), Bipolar transistor or the like.

The operation of the biosensor 10 is essentially the same as that of the biosensor 1, except that the biosensor 10 further includes the voltage amplifying part 12 for amplifying the induced voltage at the infrared absorber 3 having absorbed infrared radiation.

Figure 3:
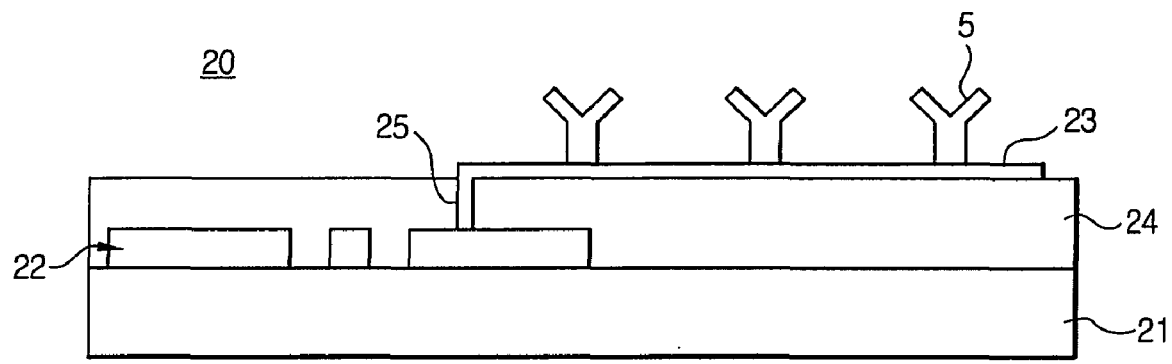
FIG. 3 is an exemplary embodiment of a cross-sectional view of a biosensor being layered on a wafer, in accordance with the present invention.

FIG. 3 illustrates another exemplary embodiment of the biosensor according to the present invention. The biosensor in this embodiment has the substantially identical structure with the biosensor shown in FIG. 2, except that the biosensor is layered on a wafer by employing the semiconductor chip fabrication method.

Referring to FIG. 3, a biosensor 20 includes a substrate 21, an infrared absorber 23, bioreceptors 5, and MOSFET 22. Since the constituents and functions thereof are substantially identical with those of the biosensor 10, only its manufacturing method will be described briefly below.

As for the substrate 21, a silicon wafer employed in a semiconductor may be used for the biosensor 20. As shown in FIG. 3, the MOSFET 22, considered the voltage amplifying part, is formed on the substrate 21. The forming may include a semiconductor fabrication process. An insulating layer 24 made of insulating substances is disposed on the MOSFET 22, and a through-hole 25 is formed in the insulating layer 24 for connecting the MOSFET 22 and the infrared absorber 23. In exemplary embodiments, the infrared absorber 23 is formed on the insulating layer 24 by following the semiconductor fabrication process. One end of the infrared absorber 23 is connected to the MOSFET 22 through the through-hole 25 formed in the insulating layer 24. Terminals (not shown) for detecting voltage are formed on the MOSFET 22 at the other end of the infrared absorber 23. The bioreceptors 5 are immobilized on the upper surface of the infrared absorber 23 to complete the manufacture of the biosensor 20.

Figure 4:
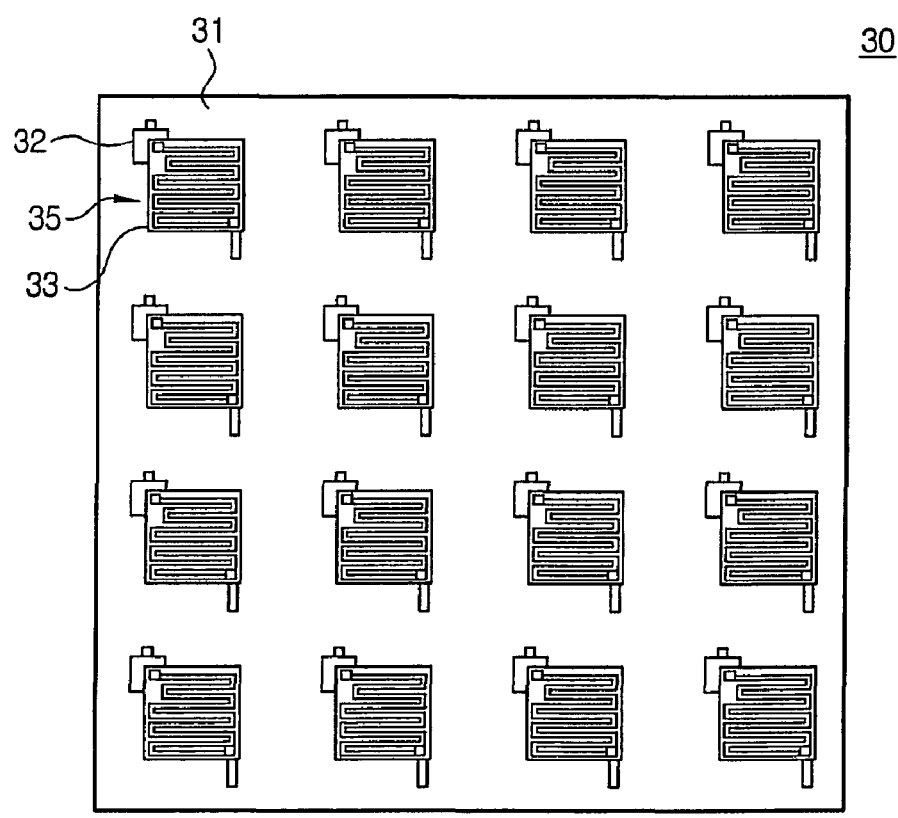
FIG. 4 illustrates an exemplary embodiment of a multi-array biosensor, in accordance with the present invention.

FIG. 4 illustrates another exemplary embodiment of the biosensor according to the present invention. In detail, FIG. 4 shows a multi-array biosensor 30 capable of simultaneously detecting different types of analytes.

A plurality of sensor units 35 are formed in grid shape on a substrate 31 of the biosensor 30. Each of the sensor units 35 has a plurality of infrared absorbers 33 formed on the substrate 31, the infrared absorbers 33 having varying resistance according to the amount of infrared radiation absorption, bioreceptors (not shown) immobilized on the infrared absorbents 33 for selectively reacting and binding with an analyte, and a voltage amplifying part 32 connected to the infrared absorbers 33 for amplifying induced voltages at the infrared absorbers 33. The biosensor 20 of FIG. 3 and each of the sensor units 35 of the biosensor 30 have the substantially same structure, except that in the biosensor 30, different types of bioreceptors (not shown) are immobilized onto the infrared absorbers 33 of the sensor units 35 to react and bind with different analytes. Also, the operation of each sensor unit 35 is essentially the same as the biosensor 20. Advantageously, the biosensor 30 may be used for detecting a diverse variety of analytes at substantially the same time using one sample. Although FIG. 4 illustrates a 4×4 multi-array biosensor 30 in a grid shape, including the sensor units 35 arranged substantially in rows and columns, the quantity and arrangement of sensor units 35 may include any of a number of configurations suitable for the purpose described herein.

Figure 5:
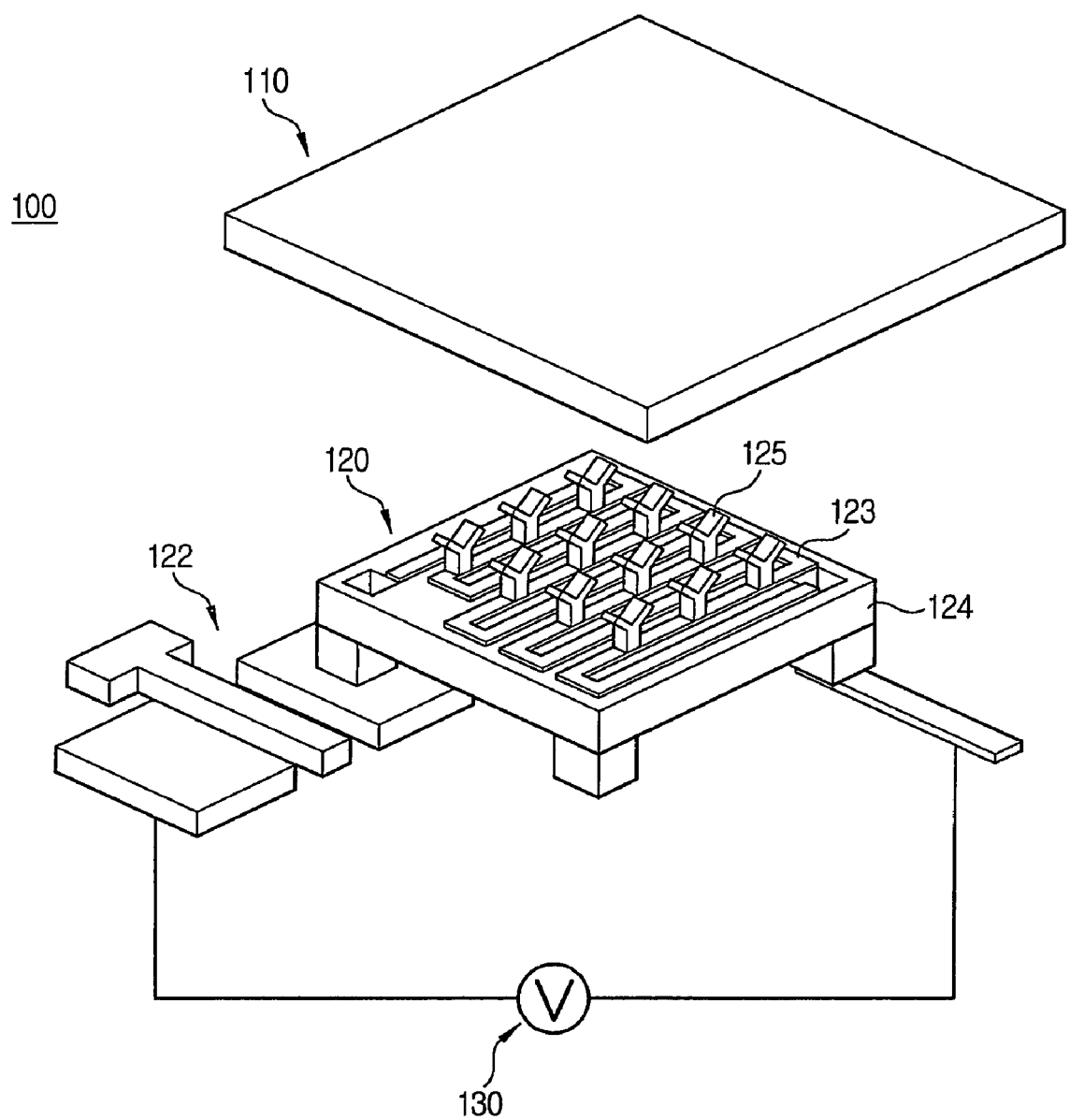
FIG. 5 is a schematic view of an exemplary embodiment of a biosensor system, in accordance with the present invention.
Figure 6:
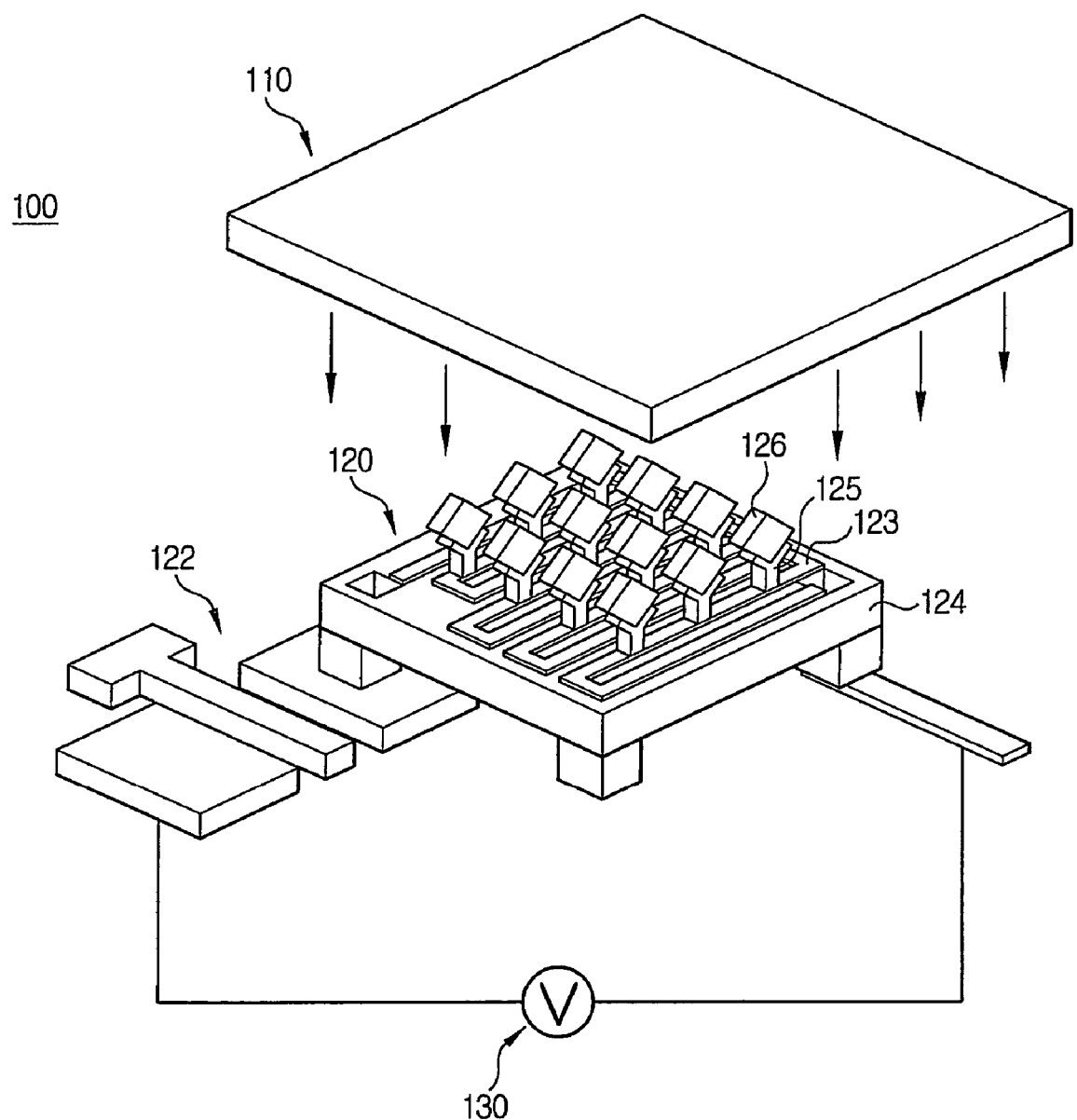
FIG. 6 is a diagram illustrating the operation of the biosensor system in FIG. 5.

FIG. 5 illustrates an exemplary embodiment of a biosensor system 100 according to the present invention, and FIG. 6 is a diagram illustrating the operation of the biosensor system 100 in FIG. 5.

Referring first to FIG. 5, the biosensor system 100 includes an infrared generator 110, a biosensor 120, and an output unit 130.

The infrared generator 110 emits infrared rays to be absorbed by an infrared absorber 123 of the biosensor 120. In exemplary embodiments, an infrared lamp may be used for the infrared generator 110. In alternative embodiments, to increase sensitivity, the infrared generator 110 may be configured to emit infrared rays having a specific wavelength range that can be well absorbed by the infrared absorber 123. In another alternative embodiment, the infrared generator 110 may also be configured to uniformly radiate infrared rays on substantially an entire area of the infrared absorber 123 of the biosensor 120.

Referring to FIG. 5, the biosensor 120 includes a support plate 124, an infrared absorber 123 on the support plate 124, having a variable resistance by the infrared radiation absorption, and bioreceptors 125 immobilized onto the infrared absorber 123 for selectively reacting and binding with an analyte. An induced voltage at the infrared absorber 123 may vary depending on whether the bioreceptor 125 has reacted and bound with the analyte. In exemplary embodiments, the biosensor 120 may further include a voltage amplifying part 122 connected to one end of the infrared absorber 123 for amplifying an induced voltage at the infrared absorber 123. The operation of the biosensor 120 is substantially the same to that of the biosensor 20 in FIG. 3, so further detailed explanation is omitted.

The output unit 130 displays an induced voltage at the biosensor 120, so that a voltage may be easily observed by a user. In exemplary embodiments, a voltmeter may be utilized for the output unit 130. In alternative embodiments, the output unit 130 may include a sensor room (not shown) to facilitate the replacement of the biosensor 120. A terminal for connecting a voltage detection terminal of the biosensor 120 may be installed in the sensor room.

The operation of an exemplary embodiment of the biosensor system of the invention will be explained with reference to FIG. 6.

A sample having an analyte 126 to be detected is coated on the surface of the biosensor 120. The surface of the biosensor 120 is irradiated by infrared rays emitted from the infrared generator 110. An output voltage is shown in the output device 130. By comparing the output voltage from the output device 130 with a reference voltage, it is determined whether the bioreceptor 125 has reacted and bound with the analyte 126. If the analyte 126 is contained in the sample, the bioreceptor 125 binds with the analyte 126 as shown in FIG. 6. The amount of infrared radiation absorbed by the infrared absorber 123 when the bioreceptor 125 binds with the analyte 126 is different from the amount of infrared radiation absorbed by the infrared absorber 123 when the bioreceptor 125 is not bound with the analyte 126 as shown in FIG. 5. If the output voltage differs from the reference voltage, it means that the bioreceptor 125 has reacted with the analyte 126. By observing the difference in the output voltage and the reference voltage, it may be concluded that the sample contains the analyte 126 to be detected. If the output voltage is equal to the reference voltage, the bioreceptor 125 has not been bound with the analyte 126. Here, it may be concluded that the sample does not contain the analyte 126 to be detected.

In exemplary embodiments, the reference voltage is obtained by immobilizing the bioreceptor 125 for use in detection of a specific analyte 126 onto the infrared absorber 123, irradiating infrared rays thereto, and finally measuring an induced voltage at the infrared absorber 123. The reference voltage may be considered to correspond to the immobilization voltage in the earlier discussed exemplary embodiment. The reference voltage may vary by the type of bioreceptor 125 and infrared absorber 123 used in the biosensor 120.

The foregoing embodiment and advantages are merely exemplary and are not to be construed as limiting the present invention. The present teaching can be readily applied to other types of apparatuses. Also, the description of the exemplary embodiments of the present invention is intended to be illustrative, and not to limit the scope of the claims, and many alternatives, modifications, and variations will be apparent to those skilled in the art.

What is claimed is:

1. A biosensor, comprising:
an infrared light source generating a light;
an infrared absorber configured to have a resistance which varies corresponding to an intensity of the light absorbed thereby, the infrared absorber being a single, indivisible and unitary component, and the infrared absorber including at least two opposing end portions;
bioreceptors immobilized onto the infrared absorber and configured to selectively react and bind with an analyte; and
a measuring unit connected to both opposing end portions of the infrared absorber and configured to measure an induced voltage of the infrared absorber, the induced voltage being due to absorption of the light by the infrared absorber,
wherein the infrared absorber induces a first voltage when the light is applied thereto when the bioreceptors are unreacted and unbound to the analyte, and
wherein the infrared absorber induces a second voltage when the light is applied thereto when the bioreceptors are reacted and bound with the analyte.

2. The biosensor according to claim 1, further comprising:
a voltage amplifying part connected to the infrared absorber and configured for amplifying the induced voltage at the infrared absorber.

3. The biosensor according to claim 2, wherein the voltage amplifying part comprises a MOSFET, Bipolar transistor, or a combination including at least one of the foregoing.

4. The biosensor according to claim 2, wherein the infrared absorber and the voltage amplifying part are layered on a wafer.

5. The biosensor according to claim 2, further comprising an insulating layer formed on the voltage amplifying part; and
 a through-hole formed in the insulating layer for connecting the voltage amplifying part to the infrared absorber, the infrared absorber being formed on the insulating layer.

6. The biosensor according to claim 1, wherein the infrared absorber comprises Ti (titanium).

7. The biosensor according to claim 1, wherein the bioreceptor comprises enzyme, antibody, antigen, membrane, receptor, cell, tissue, DNA, or a combination including at least one of the foregoing.

8. A biosensor, comprising:
 an infrared light source generating a light;
 a substrate;
 a plurality of infrared absorbers formed on the substrate, the plurality of infrared absorbers having a resistance which varies corresponding to an intensity of the light absorbed by each of the plurality of infrared absorbers, each of the plurality of infrared absorbers being a single, indivisible and unitary component;
 a plurality of bioreceptors immobilized onto the infrared absorbers, the plurality of bioreceptors being of varying types configured for selectively reacting and binding with different analytes;
 a plurality of voltage amplifying parts connected to the plurality of the infrared absorbers, for amplifying an induced voltage at each of the plurality of infrared absorbers; and
 a measuring unit configured to measure an induced voltage of the plurality of infrared absorbers, the induced voltage being due to absorption of the light by the infrared absorber,
 wherein the induced voltage at the infrared absorber varies depending on whether different kinds of bioreceptors react and bind with the analytes.

9. The biosensor according to claim 8, wherein the voltage amplifying part comprises a MOSFET, Bipolar transistor or a combination including at least one of the foregoing.

10. The biosensor according to claim 8, wherein the biosensor is layered on a wafer.

11. The biosensor according to claim 8, wherein the infrared absorber comprises Ti (titanium).

12. The biosensor according to claim 8, wherein the infrared absorber is shaped in a zigzag pattern to maximize the surface area covered by the infrared absorber and to thereby maximize infrared radiation absorption.

13. The biosensor according to claim 8, wherein the bioreceptor comprises enzyme, antibody, antigen, membrane, receptor, cell, tissue, DNA, or a combination including at least one of the foregoing.

14. The biosensor according to claim 8, further comprising a plurality of sensor units comprising the plurality of infrared absorbers and the plurality of voltage amplifying parts, the sensor units arranged in a grid pattern.

15. The biosensor according to claim 8, wherein the plurality of infrared absorbers each have a resistance varying in accordance with an amount of absorbed infrared radiation.

16. A biosensor system, comprising:
 an infrared generator generating a light;
 a biosensor including an infrared absorber which is a single, indivisible and unitary component, and which has a resistance which varies according to an amount of the light absorbed from the infrared generator, and bioreceptors immobilized onto the infrared absorber for selectively reacting and binding with an analyte, wherein, an induced voltage at the infrared absorber varies depending on whether the bioreceptor reacts and binds with the analyte; and
 an output unit for displaying the variation in the induced voltage at the biosensor due to a variation in an amount of the light absorbed thereby.

17. The biosensor system according to claim 16, wherein the biosensor further comprises:
 a voltage amplifying part connected to the infrared absorber, for amplifying the induced voltage at the infrared absorber.

18. The biosensor system according to claim 17, wherein the voltage amplifying part comprises a MOSFET, Bipolar transistor, or a combination including at least one of the foregoing.

19. The biosensor system according to claim 18, wherein the infrared absorber and the voltage amplifying part are layered on a wafer.

20. The biosensor system according to claim 16, wherein the infrared generator comprises an infrared lamp.

21. The biosensor system according to claim 16, wherein the infrared absorber comprises Ti (titanium).

22. The biosensor system according to claim 16, wherein the bioreceptor comprises enzyme, antibody, antigen, membrane, receptor, cell, tissue, DNA, or any combination including at least one of the foregoing.

23. The biosensor system according to claim 16, wherein the biosensor further comprises a support plate, the infrared absorbers formed on the support plate.

* * * * *